United States Patent [19]

Ignacio

[11] Patent Number: 6,063,631
[45] Date of Patent: May 16, 2000

[54] STERILIZATION INDICATOR

[75] Inventor: Ramon T. Ignacio, Somerville, N.J.

[73] Assignee: 3M Innovative Properties Company, St. Paul, Minn.

[21] Appl. No.: 08/859,759

[22] Filed: May 21, 1997

[51] Int. Cl.[7] .................................................. G01N 21/78
[52] U.S. Cl. .................................. 436/1; 422/28; 422/86; 422/87; 436/135
[58] Field of Search ........................ 436/1, 135; 422/86, 422/87, 28, 32

[56] References Cited

U.S. PATENT DOCUMENTS

| 3,098,751 | 7/1963 | Huyck et al. |
| 3,183,173 | 5/1965 | Oakes . |
| 3,627,469 | 12/1971 | Cheng . |

(List continued on next page.)

FOREIGN PATENT DOCUMENTS

| 0 014 447 A1 | 8/1980 | European Pat. Off. . |
| 0 069 037 A1 | 1/1983 | European Pat. Off. . |
| 0 421 760 B1 | 3/1994 | European Pat. Off. . |
| 0 707 186 A1 | 4/1996 | European Pat. Off. . |
| 2 027 604 | 5/1970 | Germany . |
| 268 396 A1 | 5/1989 | Germany . |
| 273 776 A1 | 11/1989 | Germany . |
| 90 04 818 | 4/1990 | Germany . |
| Sho. 49-46440 | 1/1974 | Japan . |
| WO 93/16386 | 8/1993 | WIPO . |
| WO 98/46994 | 10/1994 | WIPO . |
| WO 95/06134 | 3/1995 | WIPO . |
| WO 96/3344242 | 10/1996 | WIPO . |
| WO 96/40299 | 12/1996 | WIPO . |

OTHER PUBLICATIONS

Chemical Abstracts, CA 83:107905, Ono et al. Japanese Patent JP 49046440 B4 "Test Paper for Determination of Hydrogen Peroxide Content.", 1974.

Derwent Publications Ltd., JP 49 046440 B, Dec. 10, 1974 (Abstract).
Alfa et al., "Comparison of Ion Plasma, Vaporized Hydrogen Peroxide, and 100% Ethylene Oxide Sterilizers to the Dec. 1988 Ethylene Oxide Gas Sterilizer", Infection Control and Hospital Epidemiology, pp. 92–100, Feb. 1996.
Steris Process Monitoring, 612025 Rev. C, May 1995.
Advertisements of Sterrard* Chemical Indicator Strip, Advanced Sterilization Products, 1995.
Nancy G. Chobin, RN, "Cost analysis of three low–temperature sterilization systems", pp. 29–34, Journal of Healthcare Material Management, Aug. 1994.
John McCormack, "Ask these questions before buying new sterilization technologies", Materials Management, 68–69, Jun. 1994.
"Sterilization Using Gaseous Hydrogen Peroxide—Validation of the VHP™ Series 100 Endoscope Sterilizer for Sterilization of Rigid Endoscopes . . . ", Technical Report, Amsco International, Inc. Apr. 1994.
Borneff et al., On the Efficacy and Validation of $H_2O_2$ Plasma Sterilizers.
P. Mecke, "Hydrogen Peroxide Plasma—an Interesting Microbiocidal Concept", Hygiene+ Medizin, 1992: 17:537–543.
Günter Spicher, "Biological Indicators and Monitoring Systems for Validation and Cycle Control of Sterilization Processes", Zbl. Bakt. Hyg. A 267, 463–484, 1988.
Eskenazi et al., "Evaluation of Glutaraldehyde and Hydrogen Peroxide for Sanitizing Packaging Materials of Medical Devices in Sterility Testing", J. Assoc. Off. Anal. Chem. (vol. 65, No. 5) 1982.
Steris Process, Chemical Monitoring Strips for Independent Monitoring of the Steris Process, Brochure of Steris Corporation.

*Primary Examiner*—Jan Ludlow
*Attorney, Agent, or Firm*—Jeffrey J. Hohenshell

[57] ABSTRACT

A sterilization indicator includes a substrate and indicator composition. The indicator composition contains a colorant, such as acid fuchsin, that undergoes a distinct color change if exposed to hydrogen peroxide vapor. The sterilization indicator can be used to monitor a sterilization process involving hydrogen peroxide vapor.

7 Claims, 1 Drawing Sheet

U.S. PATENT DOCUMENTS

| | | |
|---|---|---|
| 3,627,698 | 12/1971 | Rey et al. . |
| 3,654,179 | 4/1972 | Bauer . |
| 3,654,180 | 4/1972 | Bauer . |
| 3,667,916 | 6/1972 | Sliva et al. . |
| 3,704,096 | 11/1972 | Verses et al. . |
| 3,862,824 | 1/1975 | Chapman . |
| 3,899,295 | 8/1975 | Halpern . |
| 4,042,336 | 8/1977 | Larsson . |
| 4,091,921 | 5/1978 | Lewis . |
| 4,098,577 | 7/1978 | Halpern . |
| 4,138,216 | 2/1979 | Larsson et al. . |
| 4,145,186 | 3/1979 | Andersen . |
| 4,155,895 | 5/1979 | Rohowetz et al. ............. 260/33.4 |
| 4,165,399 | 8/1979 | Germonprez ..................... 427/264 |
| 4,166,044 | 8/1979 | Germonprez et al. ............ 252/408 |
| 4,168,779 | 9/1979 | Yokokoji et al. . |
| 4,179,397 | 12/1979 | Rohowetz et al. ............... 252/408 |
| 4,188,437 | 2/1980 | Rohowetz ........................ 428/199 |
| 4,206,844 | 6/1980 | Thukamoto et al. . |
| 4,240,926 | 12/1980 | McNeely . |
| 4,314,344 | 2/1982 | Johns et al. . |
| 4,328,182 | 5/1982 | Blake . |
| 4,407,960 | 10/1983 | Tratnyek . |
| 4,416,984 | 11/1983 | Wheeler, Jr. . |
| 4,448,548 | 5/1984 | Foley . |
| 4,461,837 | 7/1984 | Karle et al. . |
| 4,521,376 | 6/1985 | Witonsky et al. . |
| 4,579,823 | 4/1986 | Ryder . |
| 4,596,773 | 6/1986 | Wheeler, Jr. . |
| 4,643,876 | 2/1987 | Jacobs et al. . |
| 4,671,936 | 6/1987 | Barron . |
| 4,673,635 | 6/1987 | Yamanishi et al. . |
| 4,717,661 | 1/1988 | McCormick et al. . |
| 4,741,437 | 5/1988 | Gorski et al. . |
| 4,756,758 | 7/1988 | Lent et al. ........................... 106/22 |
| 4,756,882 | 7/1988 | Jacobs et al. . |
| 4,828,797 | 5/1989 | Zwarun et al. . |
| 4,839,291 | 6/1989 | Welsh et al. . |
| 4,876,207 | 10/1989 | Mack, II et al. . |
| 4,885,253 | 12/1989 | Kralovic . |
| 4,898,762 | 2/1990 | Brown et al. ...................... 428/152 |
| 4,935,371 | 6/1990 | Rickloff . |
| 4,968,351 | 11/1990 | Ahmed et al. .................... 106/402 |
| 5,073,488 | 12/1991 | Matner et al. . |
| 5,084,239 | 1/1992 | Moulton et al. . |
| 5,087,659 | 2/1992 | Fujisawa ............................ 524/594 |
| 5,139,957 | 8/1992 | Grack . |
| 5,167,923 | 12/1992 | Van Iperen . |
| 5,260,023 | 11/1993 | Evans, II . |
| 5,316,575 | 5/1994 | Lent et al. ........................... 106/20 |
| 5,344,017 | 9/1994 | Wittrock . |
| 5,377,496 | 1/1995 | Otto et al. . |
| 5,389,336 | 2/1995 | Childers . |
| 5,451,372 | 9/1995 | Larsson et al. . |
| 5,482,684 | 1/1996 | Martens et al. . |
| 5,498,526 | 3/1996 | Caputo et al. . |
| 5,516,648 | 5/1996 | Malchesky et al. . |
| 5,518,927 | 5/1996 | Malchesky et al. . |
| 5,552,320 | 9/1996 | Smith . |
| 5,620,656 | 4/1997 | Wensky et al. . |
| 5,623,810 | 4/1997 | Dey et al. ............................ 53/425 |
| 5,709,067 | 1/1998 | Dey et al. ............................ 53/430 |
| 5,732,529 | 3/1998 | Dey et al. ......................... 53/389.2 |
| 5,882,611 | 3/1999 | Williams et al. .................. 422/292 |
| 5,887,716 | 3/1999 | Williams et al. ................ 206/459.1 |

STERILIZATION INDICATOR

BACKGROUND OF THE INVENTION

Medical instruments and parenteral drugs are sterilized prior to use. A traditional sterilization process uses steam under pressure. Alternative sterilization processes use ethylene oxide or hydrogen peroxide in vapor form as the sterilant.

Sterilization indicators are used to monitor whether a sterilization process has been performed. Sterilization indicators may include an indicator composition, carried on a substrate, that changes color during the sterilization process.

SUMMARY OF THE INVENTION

The invention features monitoring a sterilization process that uses hydrogen peroxide vapor with a colorant that chemically reacts with hydrogen peroxide. The chemical reaction causes the colorant to undergo a distinct color change during the sterilization process, providing an indication that the sterilization process has occurred. A distinct color change occurs if normal medical professionals can readily discern the color change through visual observation.

Preferably the colorant is a dye such as acid fuchsin. Acid fuchsin changes from purple to colorless when exposed to hydrogen peroxide vapor.

The invention also features a sterilization indicator for use in monitoring a sterilization process involving hydrogen peroxide vapor. The sterilization indicator includes an indicator composition, containing colorant, carried on a substrate such as a polyester strip. The indicator composition optionally may also contain a resin that binds the indicator composition to the substrate. In addition, the composition optionally may contain a second colorant that does not undergo a distinct color change during exposure to hydrogen peroxide vapor.

The invention also features the indicator composition itself. In addition, the invention features manufacturing the sterilization indicator by printing the indicator composition onto the substrate.

Other features and advantages will be apparent from the description of the drawing and the preferred embodiment thereof, and from the claims.

BRIEF DESCRIPTION OF THE DRAWING

The FIGURE is a face plan view of an embodiment of a sterilization indicator.

DESCRIPTION OF THE PREFERRED EMBODIMENTS

Figure 1:
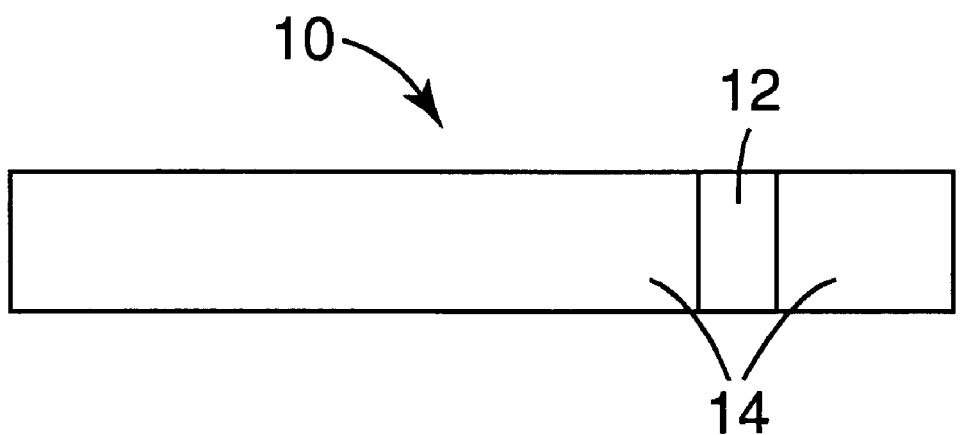

The preferred sterilization indicator includes an indicator composition and a substrate.

The indicator composition undergoes a distinct color change when exposed to hydrogen peroxide vapor. Preferably the indicator composition, after incorporation into the sterilization monitor, will exhibit the distinct color change within a certain period of time (e.g., 5 minutes, 15 minutes, or 2 hours) of exposure to an atmosphere containing at least 30% hydrogen peroxide at 45° C. The indicator composition preferably does not undergo fade if left exposed to UV light. For example, the indicator composition preferably will not fade if the sterilization indicator is exposed at a distance of several inches to a standard fluorescent light for one or two days. It also preferably does not revert to its original color when exposed to the air once the sterilization process is complete.

The preferred indicator composition contains a dye that chemically reacts with hydrogen peroxide to undergo a distinct color change. For example, the dye may change, or bleach, from purple to colorless, or from reddish purple to yellow, when exposed to hydrogen peroxide vapor. Examples of dyes that change color in response to hydrogen peroxide vapor include acid fuchsin, basic fuchsin, pinacyanole, ethyl red, and aniline blue.

Enough of the dye should be included in the indicator composition to provide the desired initial color intensity. The quantity of the dye in the composition also will influence the rate at which the composition undergoes the distinct color change. The indicator composition may contain, for example, between 0.05% and 5%, or between 0.1% and 2.5%, of the dye by weight.

Although the dye that undergoes a distinct color change in response to hydrogen peroxide vapor may be the sole colorant in the indicator composition, optionally the composition may also include a second dye that does not change color when exposed to hydrogen peroxide vapors. If the second dye is used in compositions containing a dye that becomes colorless when exposed to hydrogen peroxide, the indicator composition will not fade and become colorless during sterilization, but instead will change from an initial color to the color of the second dye. For example, if the indicator composition contains acid fuchsin, the second dye can be a green dye which in combination with acid fuchsin initially provides the composition with a purple color, but which after the acid fuchsin has become colorless because of exposure to hydrogen peroxide vapor provides the composition with a green color.

A sufficient quantity of the second dye should be included in the indicator composition to provide the targeted color intensity, both prior to and subsequent to exposure to hydrogen peroxide vapor. Too large a quantity of the second dye, for example, may overcome the color of the first dye (pre-exposure to hydrogen peroxide) in the composition. The indicator composition may include, for example, between 0.05% and 5%, or between 0.1% and 2.5% of the second dye by weight.

The indicator composition may contain a resin that binds the composition to the substrate. Examples of binder resins include shellac, ethyl cellulose, hydroxypropyl methylcellulose, methyl cellulose, and ethyl hydroxyethyl ethylcellulose. The shellac can be, for example, bleached bone dry shellac. A sufficient quantity of binder resin should be included in the composition to provide adequate binding of the composition to the substrate.

The indicator composition also may include resins that perform functions other than binding. For example, the composition may include a resin that functions as a dispersing agent that assists in dispersing the ingredients of the composition in the solvent used in application of the composition to a substrate. The composition also may include a resin that makes the composition water resistant once applied to the substrate. Examples of other indicator compositions include acrylic resins.

The binder resin and other resins in the indicator composition may influence the rate at which hydrogen peroxide vapor penetrates into the composition during the sterilization process. The rate of hydrogen peroxide penetration, in turn, may influence the rate of color change of the composition. As a result, the quantity of total resin used in the composition should be selected to provide the targeted rate of color change. The indicator composition may include, for example, between 20% and 99% of total resin by weight.

The resin may be all binder resin, or may be for example, a mixture of binder resin and other resin(s). In the latter situation, the indicator composition may contain, for example, between 30% and 70% of the binder resin by weight, and between 10% and 50% (or 20% and 40%) of the other resin(s) by weight.

The indicator composition may contain other ingredients such as opacifying agents (e.g., titanium dioxide).

Prior to application to the substrate, the indicator composition is dissolved/dispersed in a suitable solvent (e.g., water or a lower-alkyl ($C_1$–$C_4$) alcohol like ethanol or isopropyl). Generally, anywhere from one to two parts of solvent to one part of the indicator composition may be used.

The sterilization monitor preferably can be handled before and after the sterilization process without irritating the skin of the handler. Hydrogen peroxide, particularly at higher concentrations, is an irritant, and thus the preferred substrates are those that do not absorb significant quantities of hydrogen peroxide during the sterilization process. Examples of non-absorbent substrates include polyester, such as Melinex Polyester film. Examples of absorbent substrates include paper substrates, such as blotter paper.

The substrate may be in the form of a strip (e.g., 4.25× 0.62 inch) having the indicator composition at one end; the other end of the strip then can serve as a grip for the user. When the substrate is an absorbent material such as blotter paper, the grip portion of the strip may be laminated with a plastic outer surface to minimize the absorption of hydrogen peroxide by the grip during the sterilization process.

The substrate may also have an adhesive on the bottom surface that allows the sterilization indicator to be used as a label. An example of a suitable polyester label is Copycode WH®, a white polyester with a printable topcoat manufactured by the Fasson Film Division of Avery-Dennison Co.

The indicator composition may be applied to the substrate by any suitable technique. For example, the indicator composition may be applied to the substrate using conventional printing techniques such as flexographic printing or extrusion printing.

Examples 1–5 are examples of sterilization indicators.

EXAMPLE 1

An indicator composition (in solvent) was prepared that contained the following ingredients:

| Ingredient | Quantity | Supplier |
| --- | --- | --- |
| Isopropyl Alcohol (Solvent) | 300 Grams | — |
| Acrysol I-545* | 150 Grams | Rohm & Haas Co. |
| Shellac Bleached Bone Dry (V-117**) | 150 Grams | Zehrong Corp. |
| Ethanol (V-117 Solvent) | 150 Grams | — |
| Titanium Dioxide (P-23) | 25 Grams | E.T. Horn |
| Green Dye (DB-892) | 3 Grams | Colorcon |
| Acid Fuchsin | 3 Grams | Aldrich Chemical |

*Includes water.
**V-117 includes shellac bleached bone dry dissolved in ethanol.

The composition was prepared by combining the isopropyl alcohol and V-117; separately combining the acid fuchsin, the green dye, and the P-23; adding the dye/P-23 combination to the isopropanol/V-117 solution; mixing vigorously; adding the Acrysol I-545; and mixing until homogeneous.

The indicator composition was printed as a stripe on one end of a 4¼×0.625 inch strip of blotter paper using an extrusion-type printing method. Referring to the Figure, after the solvent evaporated, a sterilization indicator (10) was provided having a stripe portion (12) that includes the indicator composition, and two portions (14) consisting only of the paper substrate. The sterilization indicator was hung inside a 16 ounce jar (with a loose cap) containing 80 ml of $H_2O_2$ (31%) at a temperature of 50° C. Initially, portion (12) was purple, but the portion turned green in less than an hour.

EXAMPLE 2

A sterilization indicator was prepared that included the same indicator composition and substrate described in Example 1, except that (1) basic fuchsin was substituted for acid fuchsin, and (2) the green dye was removed. The sterilization indicator was prepared using the procedure described in Example 1. The indicator composition initially was reddish purple, but when tested according to the procedure described in Example 1 the composition turned yellow within an hour.

EXAMPLE 3

A sterilization indicator was prepared that included the same indicator composition and substrate described in Example 2, except that pinacyanole was used in place of basic fuchsin. The sterilization indicator was prepared using the procedure described in Example 1. The indicator composition initially was blue, but when tested according to the procedure described in Example 1 the composition turned colorless within 24 hours.

EXAMPLE 4

A sterilization indicator was prepared that included the same indicator composition and substrate described in Example 2, except that ethyl red was used in place of basic fuchsin. The sterilization indicator was prepared using the procedure described in Example 1. The indicator composition initially was red, but when tested according to the procedure described in Example 1 the composition turned colorless within for 24 hours.

EXAMPLE 5

A sterilization indicator was prepared that included the same indicator composition and substrate described in Example 2, except that aniline blue was used in place of basic fuchsin. The sterilization indicator was prepared using the procedure described in Example 1. The indicator composition initially was blue, but when tested according to the procedure described in Example 1, the composition turned light blue within for 24 hours.

The sterilization indicators can be used with commercially available sterilization systems that use hydrogen peroxide vapor. The sterilization process may include, for example, exposure to an atmosphere containing at least 25% hydrogen peroxide vapor for at least 15 minutes. The sterilization process may be conducted at (greater than 40°) elevated temperatures. The sterilization system may use solely hydrogen peroxide vapor as the sterilant, or may use hydrogen peroxide vapor as part of a hydrogen peroxide gas plasma sterilization process (see, e.g., EP 0 707 186 A1).

For example, the sterilization indicator can be used with the STERRARD®100 hydrogen peroxide gas plasma sterilization system, which is available from Advanced Sterilization Products, a division of Johnson & Johnson Medical, Inc. The STERRARD®100 can be used to sterilize medical instruments (e.g., fiber optic devices, endoscopic equipment, gloves, linen, parenteral drugs, etc.). The STERRARD®100 utilizes radio waves in hydrogen peroxide vapors to create a gas plasma in the sterilization chamber. Generally, the equipment to be sterilized is placed in the sterilization chamber; the chamber is evacuated; hydrogen peroxide vapor is generated in the chamber and is allowed to diffuse throughout the chamber; the gas plasma is generated in the chamber; and the chamber is evacuated. If, for example, the sterilization indicator made in Example 1 is placed in the sterilization chamber prior to the cycle, the indicator composition will convert from purple to green during the sterilization process, thereby indicating that the equipment in the chamber has been exposed to hydrogen peroxide vapor.

Other embodiments are within the claims.

What is claimed is:

1. A method of monitoring a sterilization process including the use of hydrogen peroxide vapor, comprising:

exposing an item to be sterilized and an indicator composition containing acid fuchsin to hydrogen peroxide vapor, wherein during said exposure to said hydrogen peroxide vapor, hydrogen peroxide chemically reacts with said acid fuchsin to cause a distinct color change in said indicator composition by said acid fuchsin becoming substantially colorless after chemically reacting with said hydrogen peroxide.

2. The method of claim 1, wherein said indicator composition is carried on a substrate.

3. The method of claim 2, wherein said substrate comprises a polyester strip.

4. The method of claim 1, wherein said item comprises a medical instrument.

5. The method of claim 1, wherein said item and said indicator composition are exposed to hydrogen peroxide vapor for at least 15 minutes.

6. The method of claim 5, wherein the concentration of hydrogen peroxide in said hydrogen peroxide vapor is at least 30%.

7. The method of claim 1, wherein the concentration of hydrogen peroxide in said hydrogen peroxide vapor is at least 30%.

* * * * *